United States Patent
Dabrowiak et al.

(10) Patent No.: US 10,537,465 B2
(45) Date of Patent: Jan. 21, 2020

(54) COLD PLATE DESIGN IN HEAT EXCHANGER FOR INTRAVASCULAR TEMPERATURE MANAGEMENT CATHETER AND/OR HEAT EXCHANGE PAD

(71) Applicant: Zoll Circulation, Inc., San Jose, CA (US)

(72) Inventors: Jeremy Thomas Dabrowiak, Santa Clara, CA (US); Craig Wendell Pendry, Milpitas, CA (US); Christoph Matthias Pistor, Santa Cruz, CA (US)

(73) Assignee: Zoll Circulation, Inc., San Jose, CA (US)

( * ) Notice: Subject to any disclaimer, the term of this patent is extended or adjusted under 35 U.S.C. 154(b) by 934 days.

(21) Appl. No.: 14/675,504

(22) Filed: Mar. 31, 2015

(65) Prior Publication Data

US 2016/0287434 A1  Oct. 6, 2016

(51) Int. Cl.
   *A61F 7/12* (2006.01)
   *A61F 7/00* (2006.01)
   *A61F 7/02* (2006.01)

(52) U.S. Cl.
   CPC .............. *A61F 7/12* (2013.01); *A61F 7/0085* (2013.01); *A61F 2007/0056* (2013.01); *A61F 2007/126* (2013.01)

(58) Field of Classification Search
   None
   See application file for complete search history.

(56) References Cited

U.S. PATENT DOCUMENTS

| | | |
|---|---|---|
| 1,459,112 A | 6/1923 | Mehl |
| 1,726,761 A | 9/1929 | Palmer |
| 1,857,031 A | 5/1932 | Schaffer |
| 2,223,688 A | 12/1940 | Otto |
| 2,663,030 A | 12/1953 | Dahlberg |
| 2,673,987 A | 4/1954 | Upshaw et al. |
| 2,987,004 A | 6/1961 | L |
| 3,140,716 A | 7/1964 | Harrison et al. |
| 3,224,191 A | 12/1965 | Calhoun |

(Continued)

FOREIGN PATENT DOCUMENTS

| | | |
|---|---|---|
| CN | 101090685 A | 12/2007 |
| DE | 19531935 | 2/1997 |

(Continued)

OTHER PUBLICATIONS

Jeremy Thomas Dabrowiak, Christoph Matthias Pistor, Craig Wendell Pendry, Christo Pamichev, "Fluid Cassette with Tensioned Polymeric Membranes for Patient Heat Exchange System", related pending U.S. Appl. No. 14/180,613 final office action dated Jul. 15, 2016.

(Continued)

*Primary Examiner* — Kaitlyn E Smith
(74) *Attorney, Agent, or Firm* — Fish & Richardson P.C.

(57) ABSTRACT

Cold plates through which refrigerant flows define a slot between them that can receive a cassette through which sterile working fluid with a relatively low flow rate flows from an intravascular beat exchange catheter or external pad. The slot may have bulge cavities along the edges to permit the membrane of the cassette to expand and thus establish fluid supply and return passageways.

8 Claims, 7 Drawing Sheets

(56) References Cited

U.S. PATENT DOCUMENTS

| | | |
|---|---|---|
| 3,228,465 A | 1/1966 | Louis |
| 3,369,549 A | 2/1968 | Armao |
| 3,425,419 A | 2/1969 | Actis Dato |
| 3,504,674 A | 4/1970 | Swenson |
| 3,726,269 A | 4/1973 | Webster, Jr. |
| 3,744,555 A | 7/1973 | Fletcher et al. |
| 3,751,077 A | 8/1973 | Hiszpanski |
| 3,937,224 A | 2/1976 | Uecker |
| 3,945,063 A | 3/1976 | Matsuura |
| 4,038,519 A | 7/1977 | Foucras |
| 4,065,264 A | 12/1977 | Lewin |
| 4,103,511 A | 8/1978 | Kress et al. |
| 4,126,132 A | 11/1978 | Portner et al. |
| 4,153,048 A | 5/1979 | Magrini |
| 4,173,228 A | 11/1979 | Van Steenwyk et al. |
| 4,181,132 A | 1/1980 | Parks |
| 4,181,245 A | 1/1980 | Garrett et al. |
| 4,298,006 A | 11/1981 | Parks |
| 4,459,468 A | 7/1984 | Bailey |
| 4,532,414 A | 7/1985 | Shah et al. |
| 4,552,516 A | 11/1985 | Stanley |
| 4,554,793 A | 11/1985 | Harding, Jr. |
| 4,558,996 A | 12/1985 | Becker |
| 4,581,017 A | 4/1986 | Sahota |
| 4,638,436 A | 1/1987 | Badger et al. |
| 4,653,987 A | 3/1987 | Tsuji et al. |
| 4,661,094 A | 4/1987 | Simpson |
| 4,665,391 A | 5/1987 | Spani |
| 4,672,962 A | 6/1987 | Hershenson |
| 4,754,752 A | 7/1988 | Ginsburg et al. |
| 4,787,388 A | 11/1988 | Hofmann |
| 4,813,855 A | 3/1989 | Leveen et al. |
| 4,849,196 A | 7/1989 | Yamada et al. |
| 4,852,567 A | 8/1989 | Sinofsky |
| 4,860,744 A | 8/1989 | Johnson et al. |
| 4,906,237 A | 3/1990 | Johansson et al. |
| 4,925,376 A | 5/1990 | Kahler |
| 4,941,475 A | 7/1990 | Williams et al. |
| 5,080,089 A | 1/1992 | Mason et al. |
| 5,092,841 A | 3/1992 | Spears |
| 5,103,360 A | 4/1992 | Maeda |
| 5,106,360 A | 4/1992 | Ishiwara et al. |
| 5,174,285 A | 12/1992 | Fontenot |
| 5,192,274 A | 3/1993 | Bierman |
| 5,195,965 A | 3/1993 | Shantha |
| 5,211,631 A | 5/1993 | Sheaff |
| 5,263,925 A | 11/1993 | Gilmore et al. |
| 5,269,758 A | 12/1993 | Taheri |
| 5,281,215 A | 1/1994 | Milder |
| 5,304,214 A | 4/1994 | DeFord et al. |
| 5,342,301 A | 8/1994 | Saab |
| 5,344,436 A | 9/1994 | Fontenot et al. |
| 5,370,675 A | 12/1994 | Edwards et al. |
| 5,383,856 A | 1/1995 | Bersin |
| 5,403,281 A | 4/1995 | O'Neill et al. |
| 5,433,588 A | 7/1995 | Monk et al. |
| 5,433,740 A | 7/1995 | Yamaguchi |
| 5,437,673 A | 8/1995 | Baust et al. |
| 5,458,639 A | 10/1995 | Tsukashima et al. |
| 5,466,208 A | 11/1995 | Jackson et al. |
| 5,486,207 A | 1/1996 | Mahawili |
| 5,486,208 A | 1/1996 | Ginsburg |
| 5,507,792 A | 4/1996 | Mason et al. |
| 5,531,714 A | 7/1996 | Dahn et al. |
| 5,531,776 A | 7/1996 | Ward et al. |
| 5,624,392 A | 4/1997 | Saab |
| 5,634,907 A | 6/1997 | Rani et al. |
| 5,676,670 A | 10/1997 | Kim |
| 5,693,344 A | 12/1997 | Knight et al. |
| 5,701,905 A | 12/1997 | Esch |
| 5,706,889 A | 1/1998 | Bach et al. |
| 5,709,564 A | 1/1998 | Yamada et al. |
| 5,709,654 A | 1/1998 | Klatz et al. |
| 5,716,386 A | 2/1998 | Ward et al. |
| 5,730,720 A | 3/1998 | Sites et al. |
| 5,733,319 A | 3/1998 | Neilson et al. |
| 5,737,782 A | 4/1998 | Matsuura et al. |
| 5,746,585 A | 5/1998 | McDunn et al. |
| 5,759,017 A | 6/1998 | Patton et al. |
| 5,776,079 A | 7/1998 | Cope et al. |
| 5,788,647 A | 8/1998 | Eggers |
| 5,837,003 A | 11/1998 | Ginsburg |
| 5,857,843 A | 1/1999 | Leason et al. |
| 5,862,675 A | 1/1999 | Scaringe et al. |
| 5,875,282 A | 2/1999 | Jordan et al. |
| 5,879,329 A | 3/1999 | Ginsburg |
| 5,895,418 A | 4/1999 | Saringer |
| 5,908,407 A | 6/1999 | Frazee et al. |
| 5,957,963 A | 9/1999 | Dobak, III |
| 5,980,561 A | 11/1999 | Kolen et al. |
| 5,989,238 A | 11/1999 | Ginsburg |
| 6,019,783 A | 2/2000 | Philips et al. |
| 6,042,559 A | 3/2000 | Dobak, III |
| 6,051,019 A | 4/2000 | Dobak, III |
| 6,059,825 A | 5/2000 | Hobbs et al. |
| 6,096,068 A | 8/2000 | Dobak, III et al. |
| 6,110,139 A | 8/2000 | Loubser |
| 6,110,168 A | 8/2000 | Ginsburg |
| 6,117,065 A | 9/2000 | Hastings et al. |
| 6,117,105 A | 9/2000 | Bresnaham et al. |
| 6,124,452 A | 9/2000 | Di Magno |
| 6,126,684 A | 10/2000 | Gobin et al. |
| 6,146,141 A | 11/2000 | Schumann |
| 6,146,411 A | 11/2000 | Noda et al. |
| 6,148,634 A | 11/2000 | Sherwood |
| 6,149,670 A | 11/2000 | Worthen et al. |
| 6,149,673 A | 11/2000 | Ginsburg |
| 6,149,676 A | 11/2000 | Ginsburg |
| 6,149,677 A | 11/2000 | Dobak, III |
| 6,149,806 A | 11/2000 | Baer |
| 6,165,207 A | 12/2000 | Balding et al. |
| 6,188,930 B1 | 2/2001 | Carson |
| 6,197,045 B1 | 3/2001 | Carson |
| 6,224,624 B1 | 5/2001 | Lasheras et al. |
| 6,231,594 B1 | 5/2001 | Dae |
| 6,231,595 B1 | 5/2001 | Dobak |
| 6,235,048 B1 | 5/2001 | Dobak |
| 6,238,428 B1 | 5/2001 | Werneth et al. |
| 6,245,095 B1 | 6/2001 | Dobak |
| 6,251,129 B1 | 6/2001 | Dobak et al. |
| 6,251,130 B1 | 6/2001 | Dobak et al. |
| 6,254,626 B1 | 7/2001 | Dobak |
| 6,261,312 B1 | 7/2001 | Dobak |
| 6,264,679 B1 | 7/2001 | Iwaki |
| 6,283,940 B1 | 9/2001 | Mulholland |
| 6,287,326 B1 | 9/2001 | Honda |
| 6,290,717 B1 | 9/2001 | Philips |
| 6,299,599 B1 | 10/2001 | Pham et al. |
| 6,306,161 B1 | 10/2001 | Ginsburg |
| 6,312,452 B1 | 11/2001 | Dobak et al. |
| 6,325,818 B1 | 12/2001 | Werneth |
| 6,338,727 B1 | 1/2002 | Noda et al. |
| 6,364,899 B1 | 4/2002 | Dobak |
| 6,368,304 B1 | 4/2002 | Aliberto et al. |
| 6,375,674 B1 | 4/2002 | Carson |
| 6,379,378 B1 | 4/2002 | Werneth |
| 6,383,144 B1 | 5/2002 | Mooney et al. |
| 6,383,210 B1 | 5/2002 | Magers |
| 6,393,320 B2 | 5/2002 | Lasershon |
| 6,405,080 B1 | 6/2002 | Lasershon |
| 6,409,747 B1 | 6/2002 | Gobin et al. |
| 6,416,533 B1 | 7/2002 | Gobin et al. |
| 6,419,643 B1 | 7/2002 | Shimada |
| 6,428,563 B1 | 8/2002 | Keller |
| 6,450,990 B1 | 9/2002 | Walker et al. |
| 6,461,379 B1 | 10/2002 | Carson |
| 6,464,666 B1 | 10/2002 | Augustine et al. |
| 6,464,716 B1 | 10/2002 | Dobak, III et al. |
| 6,527,798 B2 | 3/2003 | Ginsburg et al. |
| 6,530,946 B1 | 3/2003 | Noda et al. |
| 6,544,282 B1 | 4/2003 | Dae et al. |
| 6,551,309 B1 | 4/2003 | Le Pivert |
| 6,554,791 B1 | 4/2003 | Cartledge et al. |
| 6,605,106 B2 | 8/2003 | Schwartz |

(56) References Cited

U.S. PATENT DOCUMENTS

| | | |
|---|---|---|
| 6,610,083 B2 | 8/2003 | Keller et al. |
| 6,620,187 B2 | 9/2003 | Carson et al. |
| 6,620,188 B1 | 9/2003 | Ginsburg et al. |
| 6,624,679 B2 | 9/2003 | Tomaivolo et al. |
| 6,635,076 B1 | 10/2003 | Ginsburg |
| 6,635,079 B2 | 10/2003 | Ginsburg |
| 6,645,232 B2 | 11/2003 | Carson |
| 6,648,905 B2 | 11/2003 | Hoglund |
| 6,660,027 B2 | 12/2003 | Gruszecki |
| 6,669,715 B2 | 12/2003 | Hoglund et al. |
| 6,673,098 B1 | 1/2004 | Machold et al. |
| 6,679,906 B2 | 1/2004 | Hammack et al. |
| 6,685,731 B2 | 2/2004 | Kushnir et al. |
| 6,685,733 B1 | 2/2004 | Dae et al. |
| 6,692,518 B2 | 2/2004 | Carson |
| 6,695,874 B2 | 2/2004 | Machold et al. |
| 6,706,060 B2 | 3/2004 | Tzeng et al. |
| 6,716,188 B2 | 4/2004 | Noda et al. |
| 6,719,723 B2 | 4/2004 | Werneth |
| 6,719,779 B2 | 4/2004 | Daoud |
| 6,726,653 B2 | 4/2004 | Noda et al. |
| 6,740,109 B2 | 5/2004 | Dobak, III |
| 6,743,201 B1 | 6/2004 | Dönig et al. |
| 6,764,391 B1 | 7/2004 | Grant et al. |
| 6,799,063 B2 | 9/2004 | Carson |
| 6,799,342 B1 | 10/2004 | Jarmon |
| 6,802,855 B2 | 10/2004 | Ellingboe et al. |
| 6,818,012 B2 | 11/2004 | Ellingboe |
| 6,827,728 B2 | 12/2004 | Ellingboe et al. |
| 6,843,800 B1 | 1/2005 | Dobak, III |
| 6,878,156 B1 | 4/2005 | Noda |
| 6,887,263 B2 | 5/2005 | Bleam et al. |
| 6,893,419 B2 | 5/2005 | Noda et al. |
| 6,969,399 B2 | 11/2005 | Schock et al. |
| 7,070,612 B1 | 7/2006 | Collins et al. |
| 7,104,769 B2 | 9/2006 | Davis |
| 7,140,850 B2 | 11/2006 | Otis |
| 7,181,927 B2 | 2/2007 | Collins et al. |
| 7,211,106 B2 | 5/2007 | Dobak, III et al. |
| 7,377,935 B2 | 5/2008 | Schock |
| 7,510,569 B2 | 3/2009 | Dae et al. |
| 7,666,215 B2 | 3/2010 | Callister et al. |
| 7,713,036 B2 | 5/2010 | Kojima et al. |
| 7,822,485 B2 | 10/2010 | Collins |
| 7,846,193 B2 | 12/2010 | Dae et al. |
| 7,857,781 B2 | 12/2010 | Noda et al. |
| 7,892,269 B2 | 2/2011 | Collins et al. |
| 7,914,564 B2 | 3/2011 | Magers et al. |
| 8,105,262 B2 | 1/2012 | Noda et al. |
| 8,105,263 B2 | 1/2012 | Noda et al. |
| 8,105,264 B2 | 1/2012 | Noda et al. |
| 8,109,894 B2 | 2/2012 | Noda et al. |
| 8,128,384 B2 | 3/2012 | Mou |
| 8,226,605 B2 | 7/2012 | Faries et al. |
| 8,272,857 B2 | 9/2012 | Norman et al. |
| 8,888,729 B2 | 11/2014 | Noda et al. |
| 9,474,644 B2 * | 10/2016 | Dabrowiak ............ A61F 7/0085 |
| 2001/0031946 A1 | 10/2001 | Walker et al. |
| 2001/0047196 A1 | 11/2001 | Ginsburg et al. |
| 2002/0013569 A1 | 1/2002 | Sterman et al. |
| 2002/0022823 A1 | 2/2002 | Luo et al. |
| 2002/0145525 A1 | 10/2002 | Friedman et al. |
| 2002/0183692 A1 | 12/2002 | Callister |
| 2002/0198579 A1 | 12/2002 | Khanna |
| 2003/0036496 A1 | 2/2003 | Elsner et al. |
| 2003/0062090 A1 | 4/2003 | Secondo |
| 2003/0114795 A1 | 6/2003 | Durward et al. |
| 2004/0026068 A1 * | 2/2004 | Schmidt ................ A61M 5/44 165/46 |
| 2004/0089058 A1 | 5/2004 | De Hann et al. |
| 2004/0102825 A1 | 5/2004 | Daoud |
| 2004/0104018 A1 | 6/2004 | Hughes et al. |
| 2004/0143311 A1 | 7/2004 | Machold et al. |
| 2004/0210231 A1 | 10/2004 | Boucher et al. |
| 2005/0137662 A1 * | 6/2005 | Morris ............... A61B 18/1477 607/101 |
| 2005/0156744 A1 | 7/2005 | Pires |
| 2006/0064146 A1 | 3/2006 | Collins |
| 2006/0069418 A1 | 3/2006 | Schock et al. |
| 2006/0122673 A1 | 6/2006 | Callister et al. |
| 2006/0210424 A1 | 9/2006 | Mallett et al. |
| 2006/0293734 A1 * | 12/2006 | Scott .................. A61F 7/12 607/105 |
| 2007/0007640 A1 | 1/2007 | Harnden et al. |
| 2007/0076401 A1 | 4/2007 | Carrez et al. |
| 2007/0156006 A1 | 7/2007 | Smith et al. |
| 2007/0173759 A1 * | 7/2007 | Augustine ............ A61F 7/0085 604/113 |
| 2008/0082051 A1 * | 4/2008 | Miller ............. A61M 25/09041 604/164.13 |
| 2008/0119916 A1 * | 5/2008 | Choucair .................. A61F 7/10 607/104 |
| 2008/0230530 A1 | 9/2008 | Augustine et al. |
| 2008/0262409 A1 | 10/2008 | Derrico et al. |
| 2008/0267599 A1 | 10/2008 | Arnold et al. |
| 2009/0247963 A1 | 10/2009 | Bleam et al. |
| 2009/0299287 A1 | 12/2009 | Carson et al. |
| 2010/0036486 A1 | 2/2010 | Mazur |
| 2010/0082000 A1 * | 4/2010 | Honeck ............. A61M 25/0045 604/246 |
| 2010/0129248 A1 | 5/2010 | Mou |
| 2010/0256601 A1 * | 10/2010 | Lippert ............. A61M 25/0013 604/523 |
| 2011/0022136 A1 | 1/2011 | Scott et al. |
| 2011/0046551 A1 | 2/2011 | Augustine et al. |
| 2011/0137249 A1 | 6/2011 | Collins et al. |
| 2011/0184253 A1 | 7/2011 | Archer et al. |
| 2011/0208278 A1 | 8/2011 | Machold et al. |
| 2011/0213305 A1 | 9/2011 | Jönsson et al. |
| 2012/0100023 A1 | 4/2012 | Hanazuka et al. |
| 2012/0158103 A1 * | 6/2012 | Bledsoe .................. A61F 7/02 607/104 |
| 2013/0071270 A1 | 3/2013 | Zupp et al. |
| 2013/0079855 A1 | 3/2013 | Helkowski et al. |
| 2013/0079856 A1 | 3/2013 | Dabrowiak et al. |
| 2013/0178923 A1 | 7/2013 | Dabrowiak |
| 2013/0331774 A1 | 12/2013 | Farrell et al. |
| 2013/0337732 A1 * | 12/2013 | Williams ................ F24C 15/20 454/49 |
| 2014/0081202 A1 | 3/2014 | Tsoukalis |
| 2014/0094880 A1 | 4/2014 | Lim et al. |
| 2014/0094882 A1 | 4/2014 | Lim |
| 2014/0094883 A1 | 4/2014 | Lim et al. |
| 2015/0223974 A1 | 8/2015 | Dabrowiak et al. |
| 2015/0230973 A1 | 8/2015 | Dabrowiak et al. |
| 2015/0230974 A1 | 8/2015 | Pistor et al. |
| 2015/0230975 A1 | 8/2015 | Dabrowiak et al. |
| 2016/0131127 A1 | 5/2016 | Hendricks et al. |
| 2016/0287432 A1 | 10/2016 | Dabrowiak et al. |
| 2016/0287433 A1 | 10/2016 | Mazzone |
| 2016/0287434 A1 | 10/2016 | Dabrowiak et al. |
| 2016/0287435 A1 | 10/2016 | Pamichev et al. |
| 2016/0290330 A1 | 10/2016 | Pamichev et al. |
| 2017/0035604 A1 | 2/2017 | Dabrowiak |

FOREIGN PATENT DOCUMENTS

| | | |
|---|---|---|
| EP | 0663529 B1 | 5/1997 |
| GB | 2040169 | 8/1980 |
| GB | 1183185 | 2/1985 |
| GB | 2212262 | 7/1989 |
| GB | 2383828 | 7/2003 |
| JP | S61100243 A | 5/1986 |
| JP | 09-215754 | 8/1997 |
| JP | 10-0127777 | 5/1998 |
| JP | 10-305103 | 11/1998 |
| JP | 2001147095 A | 5/2001 |
| JP | 2003028582 A | 1/2003 |
| JP | 2003524507 A | 8/2003 |
| JP | 2008531114 A | 8/2008 |
| JP | 2008539034 A | 11/2008 |
| JP | 2009500066 A | 1/2009 |

(56) References Cited

FOREIGN PATENT DOCUMENTS

| | | |
|---|---|---|
| JP | 2011137621 A | 7/2011 |
| WO | 1990001682 | 2/1990 |
| WO | 1993004727 | 3/1993 |
| WO | 1994000177 | 1/1994 |
| WO | 1994001177 | 1/1994 |
| WO | 95-03680 | 2/1995 |
| WO | 1997025011 | 7/1997 |
| WO | 1998024491 | 6/1998 |
| WO | 1998040017 | 9/1998 |
| WO | 2000010494 | 3/2000 |
| WO | 2001013809 | 3/2001 |
| WO | 0126719 | 4/2001 |
| WO | 2001064146 | 9/2001 |
| WO | 2001076517 | 10/2001 |
| WO | 2001083001 | 11/2001 |
| WO | 2005117546 A2 | 12/2005 |
| WO | 2006036585 A1 | 4/2006 |
| WO | 2010040819 A1 | 4/2010 |
| WO | 2012-0175089 | 12/2012 |
| WO | 2014160422 A1 | 10/2014 |
| WO | 2015119671 A1 | 8/2015 |
| WO | 2015122938 A1 | 8/2015 |

OTHER PUBLICATIONS

Jeremy Thomas Dabrowiak, Eric Peterson, "Patient Heat Exchange System with Transparent Wall for Viewing Circulating Refrigerant", related pending U.S. Appl. No. 14/276,202 final office action dated Jul. 15, 2016.
Jeremy Thomas Dabrowiak, "Heat Exchange System for Patient Temperature Control with Multiple Coolant Chambers for Multiple Heat Exchange Modalities", related pending U.S. Appl. No. 14/175,545 non-final office action dated Feb. 12, 2016.
Jeremy Thomas Dabrowiak, Craig Wendell Pendry, Christoph Matthias Pistor, "Patient Heat Exchange System with Two and Only Two Fluid Loops", related U.S. Appl. No. 14/180,719, Non-Final Office Action dated Jun. 7, 2016.
Jeremy Thomas Dabrowiak, Christoph Matthias Pistor, Craig Wendell Pendry, Christo Pamichev, "Fluid Cassette with Tensioned Polymeric Membranes for Patient Heat Exchange System", related pending U.S. Appl. No. 14/180,613, applicant's response to non-final office action filed Jun. 1, 2016.
Christoph Matthias Pistor, Jeremy Thomas Dabrowiak, Craig Wendell Pendry, Christo Pamichev, "Fluid Cassette with Polymeric Membranes and Integral Inlet and Outlet Tubes for Patient Heat Exchange System", related pending U.S. Appl. No. 14/180,655, applicants response to non-final office action file Jun. 1, 2016.
Jeremy Thomas Dabrowiak, Eric Peterson, "Patient Heat Exchange System with Transparent Wall for Viewing Circulating Refrigerant", related pending U.S. Appl. No. 14/276,202, applicant's response to non-final office action filed Jun. 1, 2016.
Austin Reid Hendricks, Christo Petrov Pamichev, Venkata Vishnu Gurukula, Jeremy Thomas Dabrowiak, "Heat Exchange System for Patient Temperature Control with Easy Loading High Performance Peristaltic Pump", related U.S. Appl. No. 14/534,718, Non-Final Office Action dated Jul. 25, 2016.
Jeremy Thomas Dabrowiak, Craig Wendell Pendry, Christoph Matthias Pistor, "Patient Heat Exchange System with Two and Only Two Fluid Loops", related U.S. Appl. No. 14/180,719, Applicant's response to the Non-Final Office Action filed Sep. 7, 2016.
Christoph Matthias Pistor, Jeremy Thomas Dabrowiak, Craig Wendell Pendry, Christo Pamichev, "Fluid Cassette with Polymeric Membranes and Integral Inlet and Outlet Tubes for Patient Heat Exchange System", file history of related U.S. Appl. No. 14/180,655, filed Feb. 14, 2014.
Jeremy Thomas Dabrowiak, Craig Wendell Pendry, Christoph Matthias Pistor, "Patient Heat Exchange System With Two and Only Two Fluid Loops", file history of related U.S. Appl. No. 14/180,719, filed Feb. 14, 2014.

Jeremy Thomas Dabrowiak, "Heat Exchange System for Patient Temperature Control with Multiple Coolant Chambers for Multiple Heat Exchange Modalities", file history of related U.S. Appl. No. 14/175,545, filed Feb. 7, 2014.
Jeremy Thomas Dabrowiak, Eric Peterson, "Patient Heat Exchange System with Transparent Wall for Viewing Circulating Refrigerant" file history of related U.S. Appl. No. 14/276,202, filed May 13, 2014.
Austin Reid Hendricks, Christo Petrov Pamichev, Venkata Vishnu Gurukula, Jeremy Thomas Dabrowiak "Heat Exchange System for Patient Temperature Control with Easy Loading High Performance Peristaltic Pump" file history of related U.S. Appl. No. 14/534,718, filed Nov. 6, 2014.
Jeremy Thomas Dabrowiak, Christoph Matthias Pistor, Craig Wendell Pendry, Christo Pamichev, "Fluid Cassette with Tensioned Polymeric Membranes for Patient Heat Exchange System", file history of related U.S. Appl. No. 14/180,613, filed Feb. 14, 2014.
Jeremy Thomas Dabrowiak, Mark Davey, "Serpentine Heat Exchange Assembly for Removable Engagement with Patient Heat Exchange System", file history of related U.S. Appl. No. 14/675,421, filed Mar. 31, 2015.
James Mazzone, "Proximal Mounting of Temperature Sensor in Intravascular Temperature Management Catheter", file history of related U.S. Appl. No. 14/675,452, filed Mar. 31, 2015.
Christo Petrov Pamichev, Jeremy Thomas Dabrowiak, "Working Fluid Cassette with Hinged Plenum or Enclosure for Interfacing Heat Exchanger with Intravascular Temperature Management Catheter", file history of related U.S. Appl. No. 14/676,672, filed Apr. 1, 2015.
Christo Petrov Pamichev, Jeremy Thomas Dabrowiak, "Heat Exchange System for Patient Temperature Control With Easy Loading High Performance Peristaltic Pump", file history of related U.S. Appl. No. 14/676,682, filed Apr. 1, 2015.
Jeremy Thomas Dabrowiak, Christoph Matthias Pistor, Craig Wendell Pendry, Christo Petrov Pamichev, "Fluid Cassette with Tensioned Polymeric Membranes for Patient Heat Exchange System" related pending U.S. Appl. No. 14/180,613, non-final office action dated May 19, 2016.
Christoph Matthias Pistor, Jeremy Thomas Dabrowiak, Craig Wendell Pendry, Christo Petrov Pamichev, "Fluid Cassette with Polymeric Membranes and Integral Intel and Outlet Tubes for Patient Heat Exchange System", related pending U.S. Appl. No. 14/180,655, non-final office action dated May 18, 2016.
Jeremy Thomas Dabrowiak, Eric Peterson, "Patient Heat Exchange System with Transparent Wall for Viewing Circulating Refrigerant", related pending U.S. Appl. No. 14/276,202, non-final office action dated May 19, 2016.
American Urethane Inc., "Polyurethane Properties", available Oct. 12, 2010, http://web.archive.org/web/20101012211957/http://americanurethane.com/polyurethane-properties.html.
Christoph Matthias Pistor, Jeremy Thomas Dabrowiak, Craig Wendell Pendry, Christo Pamichev, "Fluid Cassette With Polymeric Membranes and Integral Inlet and Outlet Tubes for Patient Heat Exchange System", related U.S. Appl. No. 14/180,655, Final Office dated Sep. 8, 2016.
Jeremy Thomas Dabrowiak, "Heat Exchange System for Patient Temperature Control with Multiple Coolant Chambers for Multiple Heat Exchange Modalities", related pending U.S. Appl. No. 14/175,545 applicants response to non-final office action filed May 2, 2016.
F.W. Behmann, E. Bontke, "Die Regelung der Wärmebildung bei künstlicher Hypothermie", Pflugers Archiv, Bd. 266, S. 408-421 (1958).
F.W. Behmann, E. Bontke, "Intravasale Kuhlung". Pflugers Archiv, Bd. 263, S. 145-165 (1956).
Wilhelm Behringer, Stephan Prueckner, Rainer Kenter, Samuel A. Tisherman, Ann Radovsky, Robert Clark, S. William Stezoski, Heremy Henchir, Edwin Klein, Peter Safar, "Rapid Hypothermic Aortic Push Can Achieve Survival without Brain Damage after 30 Minutes Cardiac Arrest in Dogs", anesthesiology, V. 93, No. 5, Dec. 2000.
Dorraine Day Watts, Arthur Trask, Karen Soeken, Philip Predue, Sheilah Dols, Christopher Kaufman; "Hypothermic Coagulopathy in trauma: Effect of Varying levels of Hypothermia on Enzyme (56) References Cited

OTHER PUBLICATIONS

Speed, Platelet Function, and Fibrinolytic Activity", The Journal of Trauma: Injury, Infection, and Critical Care, Vo. 44, No. 5 (1998).
Simin Baharlou, "Written Opinion of the International Searching Authority", dated Oct. 12, 2017, from counterpart PCT application PCT/US2016/024970.
Wilhelm Behringer, Stephanprueckner, Rainer Kenter, Samuel A. Tisherman, Ann Radovsky, Robert Clark, S. William Stezoski, Jeremy Henchir, Edwin Klein, Peter Safar, "Rapid Hypothermic Aortic Flush Can Achieve Survival without Brain Damage after 30 Minutes Cardiac Arrest in Dogs", 200 American Society of Anesthesiologist, Inc., Anesthesiology 2000, 93:1491-9.
Jeremy Thomas Dabrowiak, Craig Wendell Pendry, Christoph Matthias Pistor, "Patient Heat Exchange System With Two and Only Two Fluid Loops", File History of related pending U.S. Appl. No. 14/180,719, filed Feb. 14, 2014.
Jeremy Thomas Dabrowiak, "Heat Exchange System for Patient Temperature Control With Multiple Coolant Chambers for Multiple Heat Exchange Modalities", File History of related pending U.S. Appl. No. 15/332,519, filed Oct. 24, 2016.
Jeremy Thomas Dabrowiak, Eric Peterson, "Patient Heat Exchange System With Transparent Wall for Viewing Circulating Refrigerant", File History of related pending U.S. Appl. No. 14/276,202, filed May 13, 2014.
Dorraine Day Watts, Arthur Trask, Karen Soeken, Philip Perdue, Sheilah Dols, Christoph Kaufmann, "Hypothermic Coagulopathy in Trama: Effect of Varying Levels of Hypothermia on Enzyme Speed, Platelet Function, and Fibrinolytic Activity"_ The Journal of Trauma, Injury, Infection, and Critical Care, vol. 44, No. 5 (1998).
Jeremy Thomas Dabrowiak, "Heat Exchange System for Patient Temperature Control with Multiple Coolant Chambers for Multiple Heat Exchange Modalities", related pending U.S. Appl. No. 14/175,545 non-final office action dated Feb. 12, 2016 (1156-117).
Jeremy Thomas Dabrowiak, Craig Wendell Pendry, Christoph Matthias Pistor, "Cold Plate Design in Heat Exchanger for Intravascular Temperature Management Catheter and/or Heat Exchange Pad", File History of related pending U.S. Appl. No. 14/675,504, filed Mar. 31, 2015. (1156-157).
Jeremy Thomas Dabrowiak, Eric Peterson, "Patient Heat Exchange System with Transparent Wall for Viewing Circulation Refrigerant", related pending U.S. Appl. No. 14/276,202, applicant's response to non-final office action filed Aug. 21, 2018. (1156-117.CIP).
Jeremy Thomas Dabrowiak, Eric Peterson, "Patient Heat Exchanger System with Transparent Wall for Viewing Circulation Refrigerant", related pending U.S. Appl. No. 14/276,202, non-final office action dated Feb. 21, 2018. (1156-117.CIP)
Jeremy Thomas Dabrowiak, Eric Peterson, "Patient Heat Exchanger System with Transparent Wall for Viewing Circulation Refrigerant", related pending U.S. Appl. No. 14/276,202, final office action dated Oct. 11, 2018. (1156-117.CIP).

\* cited by examiner

COLD PLATE DESIGN IN HEAT EXCHANGER FOR INTRAVASCULAR TEMPERATURE MANAGEMENT CATHETER AND/OR HEAT EXCHANGE PAD

TECHNICAL FIELD

The present application relates generally to heat exchange systems for patient temperature control.

BACKGROUND

Patient temperature control systems have been introduced to prevent fever in patients m the neuro ICU due to suffering from sub-arachnoid hemorrhage or other neurologic malady such as stroke. Also, such systems have been, used to induce mild or moderate hypothermia to improve the outcomes of patients suffering from such maladies as stroke, cardiac arrest, myocardial infarction, traumatic brain injury, and high intracranial pressure. Examples of intravascular heat exchange catheters are disclosed in U.S. Pat. Nos. 7,914,564, 6,416,533, 6,409,747, 6,405,080, 6,393,320, 6,368,304, 6,338,727, 6,299,599, 6,290,717, 6,287,326, 6,165,207, 6,149,670, 6,146,411, 6,126,684, 6,306,161, 6,264,679, 6,231,594, 6,149,676, 6,149,673, 6,110,168, 5,989,238, 5,879,329, 5,837,003, 6,383,210, 6,379,378, 6,364,899, 6,325,818, 6,312,452, 6,261,312, 6,254,626, 6,251,130, 6,251,129, 6,245,095, 6,238,428, 6,235,048, 6,231,595, 6,224,624, 6,149,677, 6,096,068, 6,042,559, 8,888,729, and USPPs 2013/0178923, 2013/0079855, 2013/0079856, 2014/0094880, 2014/0094882, 2014/0094883, all of which are incorporated herein by reference.

External patient temperature control systems may be used. Such systems are disclosed in U.S. Pat. Nos. 6,827,728, 6,818,012, 6,802,855, 6,799,063, 6,764,391,6,692,518, 6,669,715, 6,660,027, 6,648,905, 6,645,232, 6,620,187, 6,461,379, 6,375,674, 6,197,045, and 6,188,930 (collectively, "the external pad patents"), all of which are incorporated herein by reference. Also incorporated herein, by reference is the present assignee's U.S. patent application Ser. No. 14/276,202.

In the present assignee's U.S. Pat. No. 7,070,612, also incorporated herein by reference, a heat exchange console that could receive the coils of working fluid loops of both an intravascular heat exchange catheter and an external heat exchange pad was described and patented. In general, in all of the intravascular and external patient temperature control solutions, the temperature of the working fluid flowing through the catheter or pad is regulated by a heat exchange console based on feedback provided by the patient's actual body temperature, typically core body temperature as may be variously measured rectally, esophageally, tympanic ear temperature, blood temperature in, e.g., the vena cava, etc. The working fluid temperature is regulated by thermally coupling the working fluid to heating and/or cooling elements in the console.

SUMMARY

An apparatus includes a plate assembly having a cassette slot configured to receive a membrane assembly of a cassette, with the membrane assembly being configured for containing working fluid from an intravascular heat exchange catheter or external heat exchange pad or other modality patient heat exchange member. The plate assembly also includes rail receptacles straddling respective sides of the slot and configured for receiving respective side rails of the cassette. At least a first bulge cavity, receptacle or groove is formed inboard of a first one of the rail receptacles. The first bulge cavity may have a diameter or width at its widest point that is greater than a width of the slot.

In examples, a second bulge cavity, receptacle or groove is formed inboard of a second one of the rail receptacles. The second cavity may have a diameter or width at its widest point that is greater than a width of the slot. Both bulge cavities join with respective sides of the slot. In certain embodiments, the first and/or second bulge cavity may have a diameter or width at its widest point that is less than a transverse diameter or width of the first or second rail receptacle, and/or greater than a width of the slot.

When the cassette is engaged with the apparatus with the membrane assembly disposed in the slot and the side rails of the cassette disposed in the rail receptacles, a first portion of the membrane, e.g., near an edge of the membrane assembly, that is inboard of a side rail of the cassette can expand into the first bulge cavity when fee membrane assembly is filled with working fluid to thereby establish an enlarged fluid passageway along a vertical side edge of the membrane assembly. The first bulge cavity may extend substantially an entire length of the first rail receptacle and may be a circular or semicircular, diamond or other shape.

In another aspect, an apparatus includes a plate assembly which in turn includes a separator plate formed with a first channel on a first side of the separator plate and a second channel on a second side of the separator plate that is opposite the first side. The first channel is configured for receiving refrigerant from a compressor therethrough and the second channel is configured for receiving water or other fluid from a patient heat exchange pad or from a source of water or other fluid other than the pad. A first hacking plate abuts the first side of the separator plate and a second hacking plate abuts the second side of the separator plate. A cavity borders fee first backing plate opposite to the separator plate and is configured for receiving a cassette which is configured for holding working fluid circulating through an intravascular heat exchange catheter.

In some examples, the first and second backing plates abut the first and second sides of the separator plate along the entire or substantially the entire first and second sides of the separator plate with only the first and second channels establishing cavities through which respective fluids may flow. One or both channels may be serpentine-shaped.

With this structure, refrigerant in the first channel can exchange heat with fluid in a cassette disposed in the cavity. Likewise, refrigerant in the first channel can exchange heat across the separator plate with fluid in the second channel. Moreover, fluid in the second channel can exchange heat across the separator plate and the first backing plate with fluid in a cassette disposed in the cavity. Refrigerant flow through the first channel may be established to maintain some liquid phase throughout traversal of refrigerant through the first channel. In certain embodiments, other plate assemblies are contemplated which may have one or more channels configured for receiving water or other fluid from a patient heat exchange pad or from another source of water or other fluid (e.g., which has been cooled or heated), where the fluid or water in the channel can exchange heat with fluid in a cassette disposed in the plate assembly.

In another aspect, a heat exchange system to exchange heat with working fluid from an intravascular heat exchange catheter or from an external heat exchange pad or other modality patient heat exchange member includes at least one compressor configured to circulate refrigerant through the system to exchange heat with the working fluid. At least one duct or tube or port is configured for receiving exhaust heat from the compressor and directing the exhaust heat onto a patient.

In certain embodiments, a heat exchange system to exchange heat with working fluid from an intravascular heat exchange catheter or from an external heat exchange pad or other modality patient heat exchange member may include a plate assembly having one or more channels. A channel may be configured for receiving refrigerant therethrough, where refrigerant flow through, a channel is established or adjusted to maintain at least some liquid phase throughout, traversal of refrigerant through the channel or cold plate and the refrigerant exchanges heat with the working fluid.

The details of the various embodiments described herein, both as to structure and operation, can best be understood in reference to the accompanying drawings, in which like reference numerals refer to like parts, and in which:

DETAILED DESCRIPTION

Figure 1:
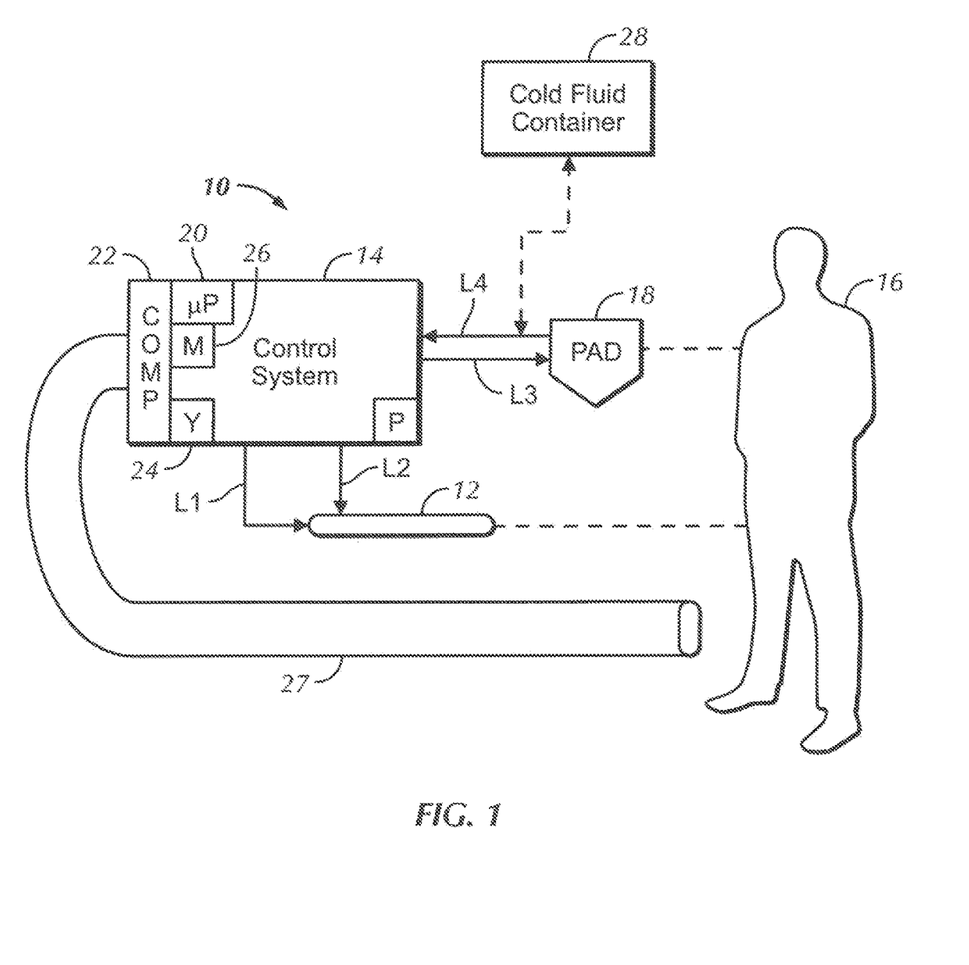
FIG. 1 is a schematic view of a non-limiting system in accordance with an embodiment.

Referring initially to FIG. 1, in accordance with present principles, a system 10 may include an intravascular heat exchange catheter 12 controlled by a control system 14 to control patient temperature, e.g., to prevent the patient 16 from becoming febrile or to induce therapeutic hypothermia in the patient 16. In the catheter, working fluid or coolant, such as hut not limited to saline circulates (typically under the influence of a pump "P" in the control system) in a closed loop from the control system 14, through a fluid supply line L1 through the catheter 12, and back to the system 14 through a fluid return line L2, such that no working fluid or coolant enters the body. Any of the catheters disclosed above or in the following U.S. patents may be used, all incorporated herein by reference: U.S. Pat. Nos. 6,419,643, 6,416, 533, 6,409,747, 6,405,080, 6,393,320, 6,368,304, 6,338,727, 6,299,599, 6,290,717, 6,287,326, 6,165,207, 6,149,670, 6,146,411, 6,126,684, 6,306,161, 6,264,679, 6,231,594, 6,149,676, 6,149,673, 6,110,168, 5,989,238, 5,879,329, 5,837,003, 6,383,210, 6,379,378, 6,364,899, 6,325,818, 6,312,452, 6,261,312, 6,254,626, 6,251,130, 6,251,129, 6,245,095, 6,238,428, 6,235,048, 6,231,595, 6,224,624, 6,149,677, 6,096,068, 6,042,559, 8,888,729, 5,486,208, 5,837,003, 6,110,168, 6,149,673, 6,149,676, 6,231,594, 6,264,679, 6,306,161, 6,235,048, 6,238,428, 6,245,095, 6,251,129, 6,409,747, 6,368,304, 6,338,727, 6,299,599, 6,287,326, 6,126,684, 7,211,106 and USPPs 2013/0178923, 2013/0079855, 2013/0079856, 2014/0094880, 2014/0094882, 2014/0094883. The catheter 12 may be placed in the venous system, e.g., in the superior or interior vena cava.

Instead of or in addition to the catheter 12, the system 10 may include one or more pads 18 that are positioned against the external skin of the patient 16 (only one pad 18 shown for clarity). The pad 18 may be, without limitation, any one of the pads disclosed in the external pad patents referenced above. The temperature of the pad 18 can be controlled by the control system 14 to exchange heat, with the patient 16, including to induce therapeutic mild or moderate hypothermia in die patient in response to the patient presenting with, e.g., cardiac arrest, myocardial infarction, stroke, high, intracranial pressure, traumatic brain injury, or other malady the effects of which can be ameliorated, by hypothermia. The pad 18 may receive working fluid from the system 14 through a fluid supply line L3, and return working fluid to the system 14 through a fluid return line 14.

The control system 14 may include one or more microprocessors 20 receiving target and patient temperatures as input and controlling, among other things, the pump "P" and a refrigerant compressor 22 and/or a bypass valve 24 that can be opened to permit refrigerant to bypass a condenser. The refrigerant circulates through a heat exchanger within the control system 14 and described further below. The processor 20 may access instructions on a computer memory 26 to configure the processor 20 to execute logic discussed below. The computer memory 26 may be, e.g., disk-based or solid-state storage.

Warm exhaust air from the compressor 22 or fan may be directed through a duet 27 to warm the patient 16. While FIG. 1 shows that the duct 27 has an open end adjacent the patient, it is to be understood that the duct 27 may direct, air into a blanket, tent, or other covering that partially or complete encloses the patient.

In other embodiments, heat, generated by the system 10, e.g., by the compressor or any other component of the system, may be transferred or directed to the surface of a patient to warm the patient before, after or while the patient is being cooled with a heat exchange catheter or pad.

FIG. 1 also shows that in the absence of refrigerant for the compressor 22 or in the absence of electrical power or other reason for not being able to circulate refrigerant through the system to cool the working fluid to the catheter 12, if it is desired to nevertheless cool the working fluid to the catheter 12 a source 28 such as a cold water bath can be connected to the pad fluid lines L3 and L4 for providing cold fluid to the system to cool the catheter working fluid. Details are discussed further below.

Figure 2:
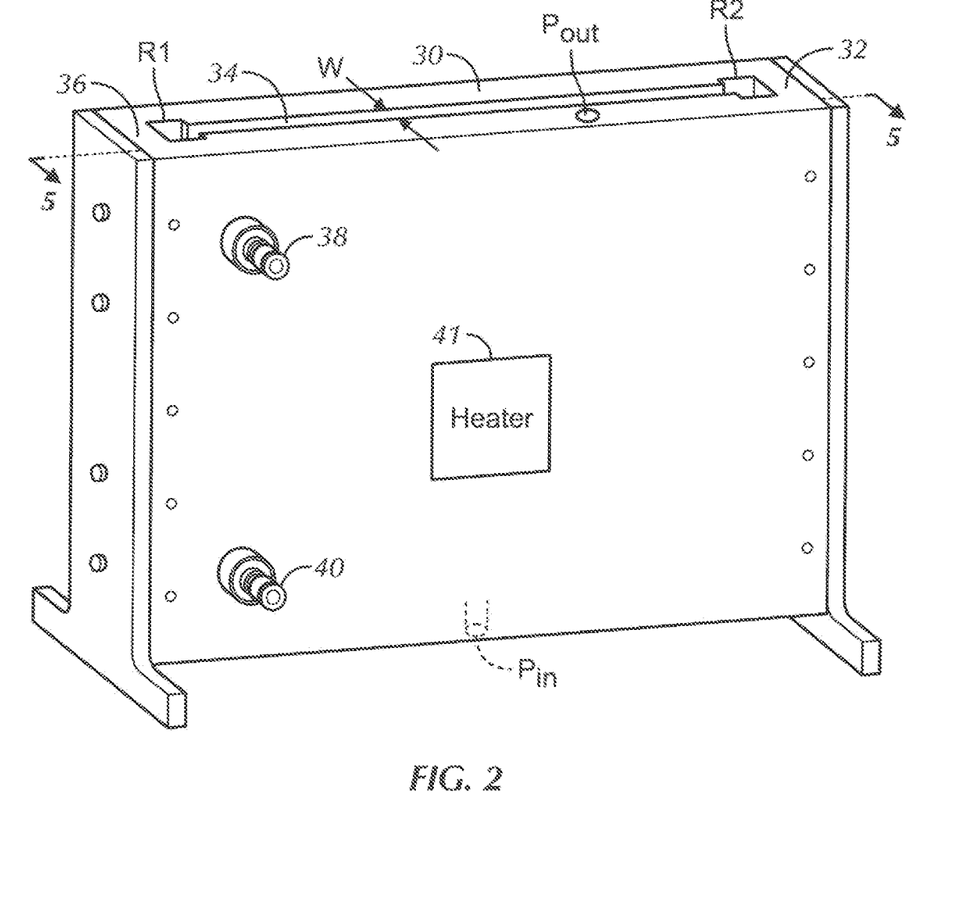
FIG. 2 is a perspective view of an example working fluid cassette holder portion of a heat exchange system.

FIG. 2 shows a portion of an example heat exchanger in the control system 14 which includes at least two cold plates 30, 32 defining a cassette slot 34 between them. In one embodiment, the width "W" of the slot 34 is less than forty mils (0.040"), and may be between twenty nine mils and thirty one mils (0.029-0.031"). In other embodiments, the slot is between 0.020"-0.070" mils. In a specific example the width "W" may be thirty mils. As further detailed below, the slot 34 may establish a coolant chamber to receive a heat exchange member such, as but not limited to a cassette through which working fluid from an intravascular heat exchange catheter, external heat exchange pad or external cooling pad or other modality patient heat exchange member flows. Because heat exchange is effected through the walls of the heat exchange member, the working fluid from the catheter or pad does not contact any surface or fluid in the heat exchanger of the control system 14 outside the walls of the heat exchange member. In this way, the working fluid, typically saline in non-limiting examples, circulating through the intravascular catheter or pad can remain sterile. Accordingly, attention will first focus on the coolant chamber established by the slot 34.

The cold plates 30,32 may be made of metal, or other thermally conductive materials, and can be rectilinear as shown and indeed may be nearly square. The cold plates 30, 32 may abut each other along left and right side walls 36, with elongated vertical cassette frame receptacles R1 and R2 being located immediately inboard of the respective side walls 36 and with the slot 34 extending between the walls 36 and terminating at the receptacles R1, R2 as shown. The frame receptacles R1, R2 may be wider than the slot 34. In the example shown, refrigerant Inlet and outlet, tubes 38,40 extend through at least one of the cold plates 32 to communicate refrigerant from the compressor 22 into a refrigerant passageway in the cold plate, which establishes a second coolant chamber in addition to (and in thermal contact with) the first coolant chamber established by the slot 34. Each cold plate may have its own refrigerant inlet and outlet tubes, or each cold plate may have either an inlet or an outlet, e.g., where refrigerant passageways of the cold plates are in fluid communication with one another, or, in the embodiment shown, only one cold plate may be formed with refrigerant inlet and outlet tubes and the other cold plate either thermally coupled to the cold plate in which the refrigerant flows and/or receiving refrigerant from the other cold plate through passageways formed through one or both of the side walls 36.

In one example, pad working fluid inlet and outlets $P_{in}$ and $P_{out}$ may also be formed in at least one of the cold plates as shown. As discussed in greater detail below, working fluid from the pad 18 or from the cold fluid source 28 via lines L3 and L4, or other lines, may be ported into the pad working fluid inlet and outlets $P_{in}$ and $P_{out}$ to exchange heat with the refrigerant or in some cases with the working fluid from the catheter flowing through the cold plates. Also, to provide for warming working fluid, one or more electric heaters 41 may be mounted on one or both of the cold plates to heat the cold plates. Alternatively to warm, the cold plates, the bypass valve 24 (FIG. 1) may be opened to allow hot gaseous refrigerant from the compressor to bypass the condenser as the gaseous refrigerant circulates through the system.

Figure 3:
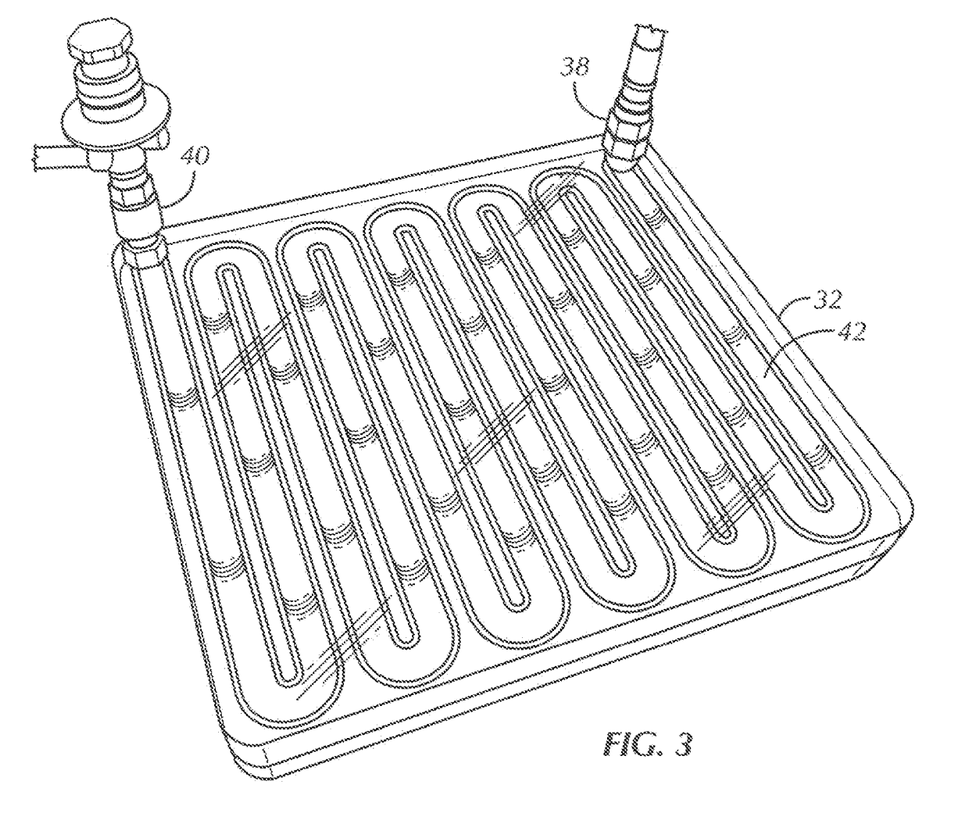
FIG. 3 is a perspective view of one half of the cassette holder shown in FIG. 2, with the opaque metal inner surface shown in transparency to reveal the serpentine refrigerant passageway.

FIG. 3 shows details of an example cold plate 32 looking at the inner surface in transparency, it being understood that the inner surface typically is metal and that the serpentine refrigerant passageway 42 shown in FIG. 3 typically would not be visible to the human eye. In any case, the example refrigerant passageway that fluidly connects the refrigerant inlet 38 to the refrigerant outlet 40 may be serpentine-shaped as shown, or may be some other shape or pattern such as a herringbone pattern, a wave pattern, or a winding, tortuous, or sinuous pattern or a configuration having one or more curves, turns and/or bends, etc.

Figure 4:
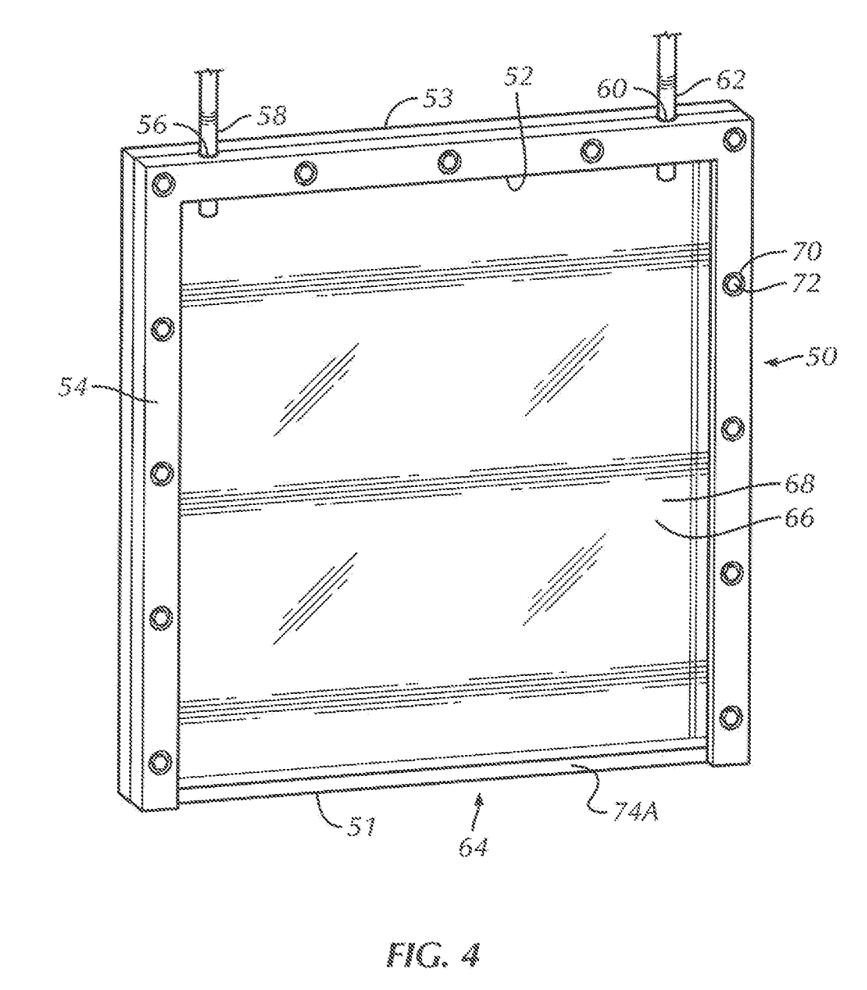
FIG. 4 is a perspective view of an example working fluid cassette configured to engage the cassette holder shown in FIGS. 2 and 3.

FIG. 4 shows an example working fluid cassette 50 according to present principles. The cassette 50 is configured to fit snugly Into the slot 34 and cassette frame receptacles R1, R2 defined between the cold plates 30,32. Working fluid such as saline from a patient-engageable heat exchange member such as the catheter 12 or external pad flows through the cassette 50 in operation, with the working fluid exchanging heat with the refrigerant in the cold plates. In example embodiments, the cassette 50 is a low cost single-use disposable item that can contain, e.g., sterile saline which circulates through the catheter 12 or an external pad. The cassette may be placed by a medical caregiver in the slot 34 between the cold plates 30,32 and the membrane portion which defines a space or working fluid chamber through which the example saline flows inflates when the working fluid flows through it, achieving thermal contact with the cold plates 30, 32.

In the example shown, the cassette 50 includes a frame 52 defining a periphery and a preferably rectilinear opening bounded as shown on at least three sides by the periphery of the frame, in the non-limiting example shown, the frame includes an elongated parallelepiped-shaped top rail 53 and elongated parallelepiped-shaped left and right side rails 54 parallel to each other and perpendicular to the top rail 53. The example frame 52 may have a metal strip or bottom rail 51 opposite the top rail and connected to the left and right side rails 54 to support the membrane and facilitate placing the membrane in biaxial tension. In any case, the example frame 52 is rectilinear and is configured for being closely received between the two cold plates 30,32, with the side rails 54 slidably engageable with the frame receptacles R1, R2 between the cold plates 30,32 and with the below-described membrane assembly passed through the slot 34 to be in close juxtaposition with the refrigerant channels in the cold plates. In certain variations, the receptacles R1, R2 may be keyed or each have a different shape which corresponds to the shapes or configuration of the side rails of the cassette. This would help ensure that the cassette is inserted into the slots and receptacles in the correct orientation, providing guidance to a user.

In FIG. 4, the frame, in the example shown, the top rail 53 thereof, is formed with a fluid inlet 56 in winch an inlet tube 58 has been disposed and a fluid outlet 60 its which an outlet tube 62 has been disposed. Both the inlet and outlet establish respective fluid passageways through the frame into the opening. The inlet and outlet tubes 58, 62 may be engaged with the fluid return and supply lines L1, L2 that are associated with the catheter 12. One or both tubes 58, 62 may terminate at just below the top rail 53 (FIG. 4), be flush with the bottom of the top rail, or they may extend any desired length down to the bottom of the assembly, i.e., one or both tubes 58,62 may extend almost the entire length of the left and right side rails 54, ending just above the below-described bottom seam of the membrane assembly. In certain embodiments, the inlet and outlet tubes may extend a length sufficient to allow the tubes to engage features or components in or on the cold plates, e.g., at least a portion or end segment of the tubes may rest in grooves or steps located in or on an inner wall or face, of the cold plate. The inlet and outlet tubes may be positioned such that they mate or are in line with bulge cavities in the cold plates. This orientation may help minimize or prevent the membrane assembly from bulging outwards in an uncontrolled or less controlled manner, which could result in a rupture. In certain embodiments, the inlet and outlet tubes 58,62 or separate inlet and outlet, tubes may be engaged with the fluid return and supply lines L3, L4 that are associated with the external pad.

Indeed, a membrane assembly 64, e.g., a polymeric membrane assembly, is connected to the frame 52, blocking the opening that is bounded on four sides by the frame as shown. The membrane assembly 64 includes a first membrane 66 that is parallel to and closely spaced from a second membrane 68, leaving a space therebetween which establishes a working fluid chamber. The fluid inlet 56 and fluid outlet 60 communicate with the space between the membranes 66,68. At least one and preferably both of the membranes 66,68 are disposed in tension in the opening. The space between the membranes is expandable when filled with working fluid.

In one example, each membrane is no more than two mils (0.003") thick and more preferably is between one mil and three mils in thickness (0.001"-0.003"), inclusive. In certain embodiments, each membrane may be between one mil and five mils in thickness (0.001"-0.005"). The example membranes 66,68 are co-extensive with the opening and like the opening are more or less square, with the length of top and bottom edges of the example membranes being approximately equal (within ±10% and more preferably within ±5%) of the lengths of the left and right edges of the membranes. In other embodiments instead of a square (1:1)) aspect ratio, an aspect ratio of up to 1:1.5 may be used. The working fluid chamber between the membranes is also rectilinear and in certain embodiments no obstructions exist between the membranes, meaning the working fluid chamber is a complete rectilinear, more or less square chamber.

Owing to the thinness of the membranes 66,68 and the closeness of the cold plates 30,32 to each other and to the membrane assembly between them when the cassette is engaged with the cold plates, the system shown in the figures affords low impedance of heat transfer between the refrigerant circulating in the cold plates and the working fluid circulating between the membranes 66, 68. The working fluid chamber between the membranes inflates due to backpressure generated by working fluid flow, eliminating or reducing the need for a moving mechanism in the cold plates. Moreover, the narrow slot 34 between the two cold plates provides better heat transfer by reducing the conductive path length between the cold plates and the working fluid. The frame allows for ease of handling, such as insertion and removal of the cassette with/from the cold plates.

With respect to the example working fluid chamber between the membranes 66,68 having a width-to-length aspect ratio near 1:1 (i.e., square or nearly so), the amount of backpressure required to induce working fluid flow through heat exchanger is reduced compared to a less square configuration. This reduces the amount of work that a working fluid pump must perform, which is desirable for two reasons. One, since the pump may be disposable, lower performance requirements translate into a lower cost disposable and quieter system. For instance, peristaltic roller pumps offer quiet operation and a low-cost disposable element, but operate most efficiently when only modest pressures are required. Two, lowering the working fluid pump work reduces the amount of heat transferred into the working fluid by the pump itself. Also, a low width/length aspect ratio results in slower working fluid velocity which reduces the amount of mixing, but this otherwise desirable (from a heat exchange standpoint) effect is negligible in the present example system since the Reynolds numbers are typically <1000, suggesting a laminar flow regime. Furthermore, a low width/length aspect ratio significantly reduces the number of bends (or "corners") in the fluid flow path. These bends are areas of mixing for the fluid which promotes beat transfer. Without them, a fluid boundary layer builds up. However, this effect is offset herein by maintaining a narrow slot between the cold plates. This way the primary heat transfer mechanism is by conduction, but the conduction path length (and therefore boundary layer) is small, resulting in a relatively high rate of heat transfer.

In certain embodiments, the surface of the cold plate facing the cassette membrane may be coated with a non-stick ("release"), and/or hydrophobic coating to aid in the removal of the cassette after use. Removal may be difficult in some instances due to backpressure from the saline fluid flow pressing the heat exchange membrane against the cold plate surface for an entire duration of use (e.g., up to 7 days), resulting in the membrane sticking to the cold plate. The large surface area may result in high farces which may be difficult for the user to overcome. Additionally, a thin film of water may exist between the membrane and cold plate surface (due to leakage, condensation), resulting in an additional capillary force which in some cases can be difficult to overcome and can result in damage to the cassette or cold plate, making extraction difficult. The non-stick and/or hydrophobic coating mitigates this by minimizing the capillary force. Additionally this water film may dry out completely, potentially resulting in van der Waals adhesion. The non-stick aspect of the coating prevents this from happening. Fluoropolymer coatings provide both hydrophobic and release (non-stick) characteristics, and may be utilized along with other non-stick and/or hydrophobic materials or coatings.

In certain examples, the membranes 66,68 are stretched under tension during assembly to the frame, preferably biaxially (i.e., in tension between the top and bottom rails 53, 51 and also in tension between the left and right side rails 54). This tension can be maintained over the shelf life of the product. Pretensioning minimizes wrinkles in material, which is beneficial because wrinkles can impede working fluid flow and create air gaps which reduce heat transfer between the working fluid and cold plates. Wrinkles can also complicate insertion of the membrane assembly into the narrow slot 34.

To establish pre-tensioning of the membranes, the frame may be made in halves and posts, such as threaded fasteners, can extend transversely to one half of the frame, with the membranes 66,68 being stretched over the posts and holes made in the membranes to receive the posts. The other half of the frame is then positioned to sandwich a rectilinear border portion of the membrane assembly between the frame halves, and a closure such as respective nuts engaged with, the posts to hold the frame halves together with the membrane assembly held in tension between the frame halves. Optionally a post, e.g., a post that uses a press fit, may be located in one or more frames to hold the frame halves together. The post may be made of plastic or other suitable material. FIG. 4 shows that the working fluid chamber is closed off at the bottom by a bottom seam 74A of the membrane assembly, which is part of the border portion. In addition to applying tension to avoid wrinkling during use, additional posts may be used to avoid wrinkling during the welding process, improving the quality of the weld joints.

In the border portion, at least one and preferably more layers of polymer film may be used to reinforce the membranes 66, 68 to establish welded seams through which (at the skies of the membrane assembly) the post holes are formed, allowing for easier fabrication. By placing reinforcing layers on the border portion only, the central "window" of the membrane assembly consists only of a single thin layer membrane between the working fluid and one of the cold-plates 30, 32 to minimize impeding heat transfer. A die-cut reinforcement layer may be used which reinforces the entire perimeter with one piece of material.

In some examples, the polymer membranes 66,68 are highly stretchable, at least greater than 25% elongation. This allows the membranes to change from the empty flat state shown in FIG. 4 to an inflated shape (within the slot 34 between the cold plates) without wrinkling. It also allows the membranes to easily conform to features on the faces of the cold plates.

Additionally, the membranes may be made of a material which can also be made into tubing. Tubes such as the inlet and outlet tubes 58, 62 shown in FIG. 4 can then be thermally welded (e.g., using RF sealing) to the membranes, which is more reliable and quicker than adhesive bonding. The membranes 66,68 need not provide their own lateral support because the cold plates 32,34 and frame 52 provide the support for the inflated membrane assembly, allowing it to withstand the pressure generated as a result of working fluid flowing through between the membranes. Structural features such as raised bumps, concavities, raised ribs, and so on may be located on the cold plates to optimize heat transfer. For example, the face of the cold plate, may be corrugated or include features (cut out or raised) that provide an increased surface area and increase or optimize heat exchange or transfer between the membranes and the cold plates. The features may have different shapes or patterns, e.g., a serpentine, winding, tortuous, or sinuous pattern or shape, or may include a configuration having one or more curves, turns and/or bends. This can be economically advantageous because the cold plates may be reusable components. Manifolds can be cut into the cold plates to even out the distribution of saline flow.

Figure 5:
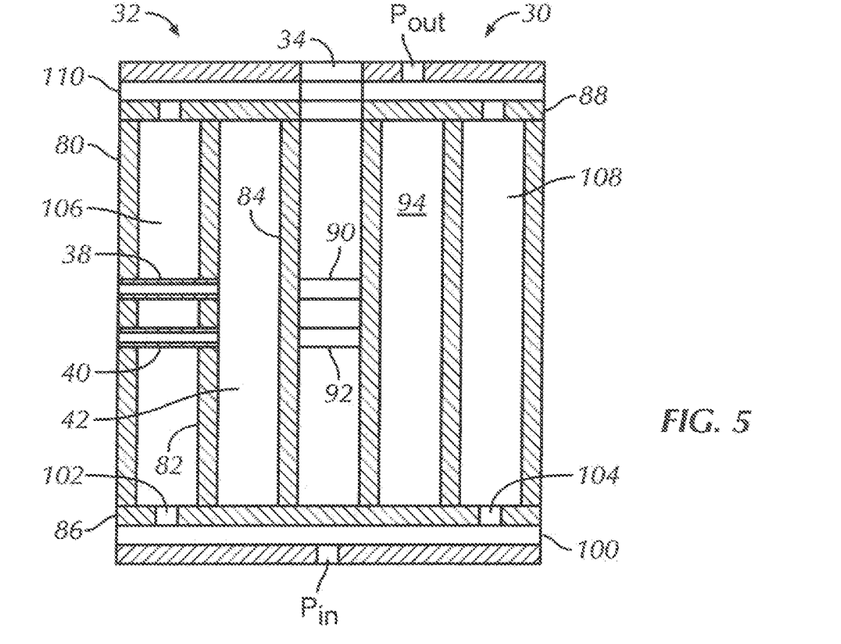
FIG. 5 is a cross-sectional view of FIG. 2.

Having described an example non-limiting thermal exchange combination of structure between the heat exchanger in the control system 14 and the sterile working fluid in the intravascular temperature control catheter 12 or pad 18, attention is now directed to FIG. 5, which shows an example embodiment of additional coolant chambers in the cold plates by which to effect heat exchange with working fluid, including non-sterile working fluid, from the external heat exchange pad 18. Note that the plate structures shown in FIG. 5 preferably are metal or other material with high heat conductivity.

As shown, the cold plates 30, 32 may be multi-plate assemblies defining multiple fluid chambers, although in the discussion below they are referred to generally as "plates" 30 and 32. In the non-limiting example shown, the refrigerant inlet and outlet tubes 38,40 extend through an outer wall 80 find a separator wall 82 of the cold plate 32 to communicate refrigerant from the compressor 22 into the refrigerant passageway in the cold plate, which establishes a refrigerant chamber 42 that is bounded by the separator wall 82 and an inner wall 84. On the other side of the inner wall 84 is the working fluid cassette slot 34. As stated earlier, each cold plate may have its own refrigerant inlet and/or outlet tubes, or only one cold plate may be formed with refrigerant inlet and outlet tubes and the other cold plate either thermally coupled to the cold plate in which the refrigerant flows and/or receiving refrigerant from the other cold plate through, passageways formed between the cold plates. In the example shown, the cold plates 30, 32 are thermally coupled through the side walls 36 (FIG. 2), a common bottom wall 86 (FIG. 5), and through the uninterrupted portions of a top wall 88 in which the slot 34 is formed.

In some examples, the cold plates 30,32 are mirror image structures of each other. In the example of FIG. 5, the refrigerant chamber 42 in the left-hand cold plate (32) is in fluid communication through refrigerant supply and return passageways 90, 92 with a refrigerant chamber 94 in the right-hand cold plate 30, Thus, the refrigerant chambers of the cold plates straddle the cassette slot 34 and are separated therefrom by respective inner walls 84, with refrigerant flowing serially through the left and right refrigerant chambers 42,94, first from the refrigerant inlet tube 38 into the left refrigerant chamber 42, then through the refrigerant supply passageway 90, the right hand refrigerant chamber 94, back through the refrigerant return passageway 92, and out the refrigerant outlet tube 40, This increases the refrigerant fluid flow rate through the refrigerant chambers 42, 94, when two refrigerant chambers are provided as in the example shown.

In contrast, pad working fluid channel fluid flow may be plumbed in parallel to left and right pad fluid chambers 106, 108, which straddle the refrigerant chambers as shown and are separated therefrom by respective separator walls 82. In the non-limiting example shown, fluid from the external pad flows through the pad working fluid inlet $P_{in}$ into an inlet plenum 100 formed in the bottom wall 86. The fluid flows in parallel through inlet ports 102, 104 into left and right pad working fluid chambers 106, 108, The fluid exits the pad working fluid chambers through an upper plenum 110 formed in the top plate 88 and out of the working fluid outlet $P_{out}$ back to the external pad. This example parallel fluid flow reduces backpressure in the pad working fluid system.

Note that the above-described series fluid flow through the refrigerant chambers and parallel flow through the pad working fluid chambers is exemplary only, and is not limiting, Thus, fluid flow through the pad working fluid chambers may be in series and/or fluid flow through the refrigerant chambers may be parallel. Note further that the particular example plumbing arrangements illustrated and described are but one example of plumbing fluid through the multi-chamber cold plates 30, 32.

Figure 6:
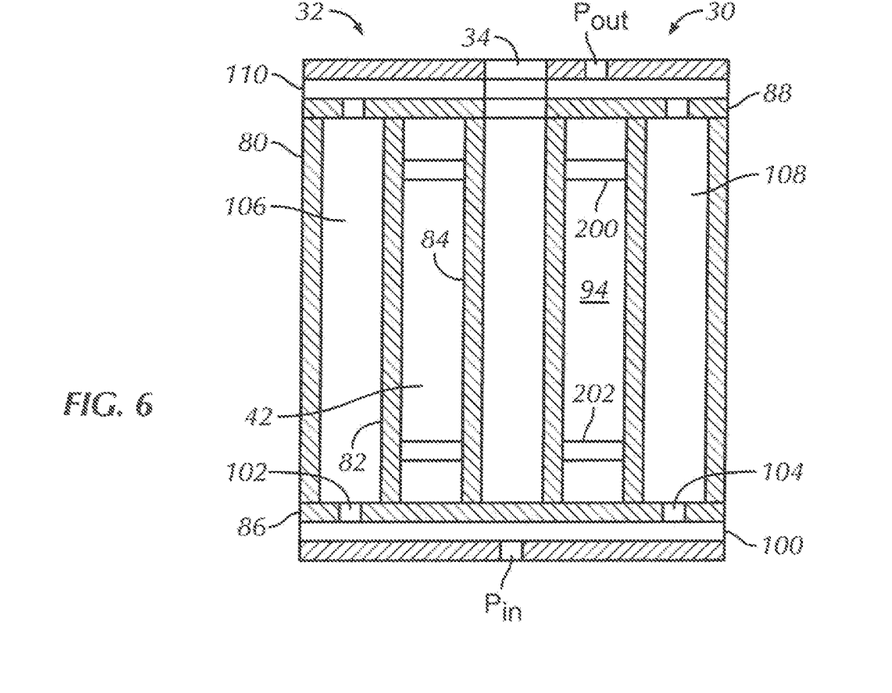
FIG. 6 is a cross-sectional view of an alternate embodiment as would be seen along the line 5-5 in FIG. 2.

Indeed, FIG. 6 shows a system similar to the one shown in FIG. 5, except that fluid flow through the refrigerant chambers is in parallel. Both refrigerant chambers may communicate with a refrigerant inlet plenum 200 through which refrigerant flows into each refrigerant chamber 42, 94 in parallel. Also, both refrigerant chambers may communicate with a refrigerant outlet plenum 202 through which refrigerant flows out of each refrigerant chamber 42, 94 in parallel back to the compressor.

It may now be appreciated that in the intravascular heat exchange mode, working fluid from the catheter 12 flowing through the cassette 50 which is disposed in the slot 34 exchanges heat with the refrigerant in the refrigerant chambers 42,94 through the respective inner walls 84. The catheter working fluid comes into contact with no portion of the cold plate heat exchanger, owing to it flowing through the cassette 50. In this way, the catheter working fluid retains its sterility and is enclosed in a closed fluid circuit for withstanding circulation fluid pressures of, e.g., up to seventy pounds per square inch (70 psi).

On the other hand, since pad working fluid is separated from the patient by an external pad, it may not require sterility, in which ease the pad working fluid may contact the separator plates 82 directly in the cold plates 30,32 to exchange heat with the refrigerant in the refrigerant chambers 42,94.

Figure 7:
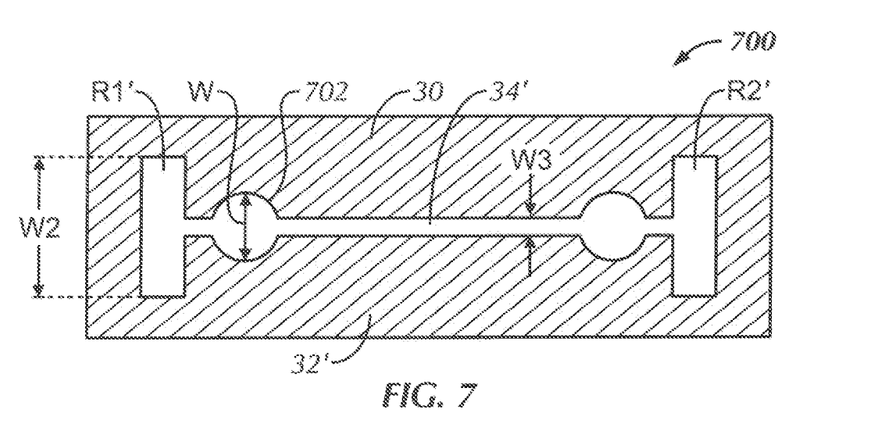
FIG. 7 is a top view of an alternate configuration for the cassette slot shown in FIG. 2.

FIG. 7 shows an alternate cold plate assembly 700 having a cassette slot 34' and rail receptacles R1' and R2' straddling the slot 34' for receiving the side rails of the cassette 50, with the receptacles and slot being substantially the same in configuration and function as the counterparts shown in FIG. 2. However, unlike FIG. 2, FIG. 7 shows that inboard of each receptacle R1', R2' the cold plate assembly 700 is formed with respective bulge or expansion cavities 702 receptacles or grooves that may extend substantially the entire length of the side rail receptacles (give or take a few millimeters). In the embodiment, each bulge cavity 702 may be circular or semicircular-shaped (although other shapes may be used). The bulge cavity may be defined between the cold plates 30', 32'. Cold plates 30' and/or 32' may have a cavity or groove formed on its inner wall. The cavity or groove may be separated or spaced apart from the side rail receptacle, e.g., by a landing or other segment of the cold plate, such that the bulge cavity is separated or spaced apart from the side rail receptacle. This may help minimize or prevent expansion of the membrane assembly into the side rail receptacles when the membrane is filled with working fluid. The bulge cavity joins or connects to the slot 34', e.g., a semicircular shaped bulge cavity may join the slot 34', at the apex of the semi-circle. As shown in FIG. 7, each bulge cavity 702 may have a width W or diameter at its widest point (e.g., the diameter of a circle or semi-circle) that is less than the transverse diameter or width W2 of the rail receptacle but greater than, the width W3 of the slot 34'. In other embodiments, the bulge cavity may be immediately inboard of a rail receptacle.

With, this structure, when the cassette 50 is engaged with the cold plate assembly 700 with the membrane assembly 64 disposed in the slot 34' and the rails of the cassette disposed in the rail receptacles R1', R2', portions of the membrane assembly, e.g., portions that are near the edges of the membrane assembly 64 and that are inboard of the side rails of the cassette, can expand into the bulge cavities 702 when the membrane assembly 64 is filled with working fluid. This establishes enlarged fluid supply and return passageways along the vertical side edges of the membrane assembly 64. In this way, working fluid entering the top of the cassette 50 along one of the side rails flows mostly down the fluid supply passageway of the portion of the membrane assembly that has expanded within the bulge cavity. The fluid supply tube on the cassette 50 may be positioned such that it is concentric with or in line with the bulge cavity. Portions of the supply fluid progressively emerge as the fluid flows down the supply passageway from the fluid supply passageway, flowing across the membrane assembly to the fluid return passageway that is established by the portion of the membrane assembly that has expanded within the bulge cavity 702 immediately adjacent the fluid return tube on the cassette 50.

Figure 8:
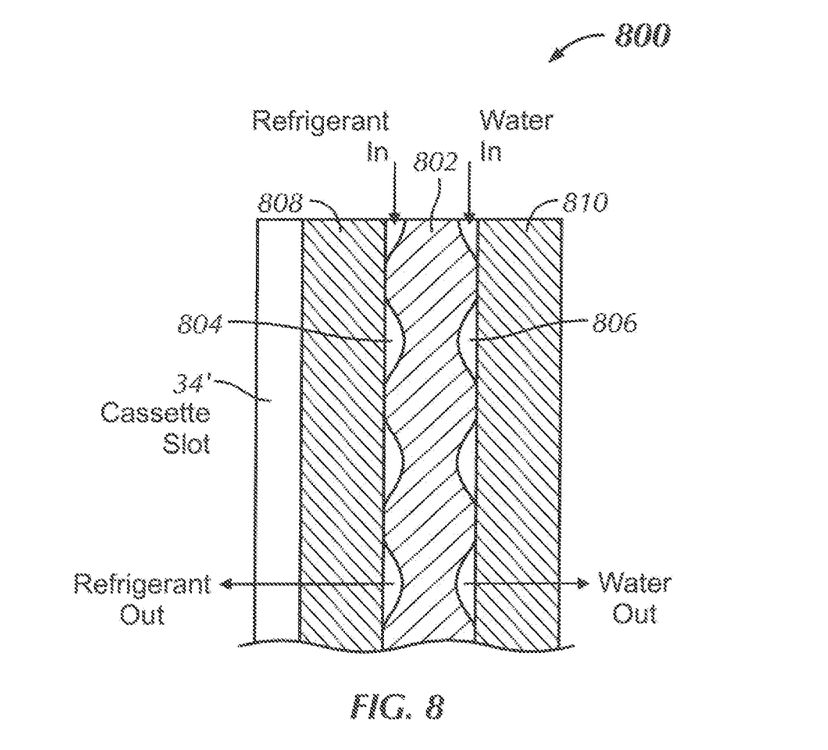
FIG. 8 is a cross-sectional view of an alternate cold plate embodiment in which refrigerant flows through concave channels on one side of a separator plate and external cooling pad water or water from a source of cold fluid flows through concave channels on the opposite side of the separator plate.

FIG. 8 illustrates an alternate cold plate 800 that is substantially identical in configuration and operation to the cold plates shown in FIGS. 5 and 6, with the following exceptions, A separator plate 802 may have channels 804, 806 (that may be configured like the serpentine channel 42 shown m FIG. 3 or configured in another pattern or shape, e.g. having one or more curves, turns and/or bends) formed in each of its respective side surfaces. Like the other cold plate structures shown and discussed herein, the separator plate 802 is highly thermally conductive and may be made of metal or an appropriate thermoplastic or other heat-transmitting material.

Figure 9:
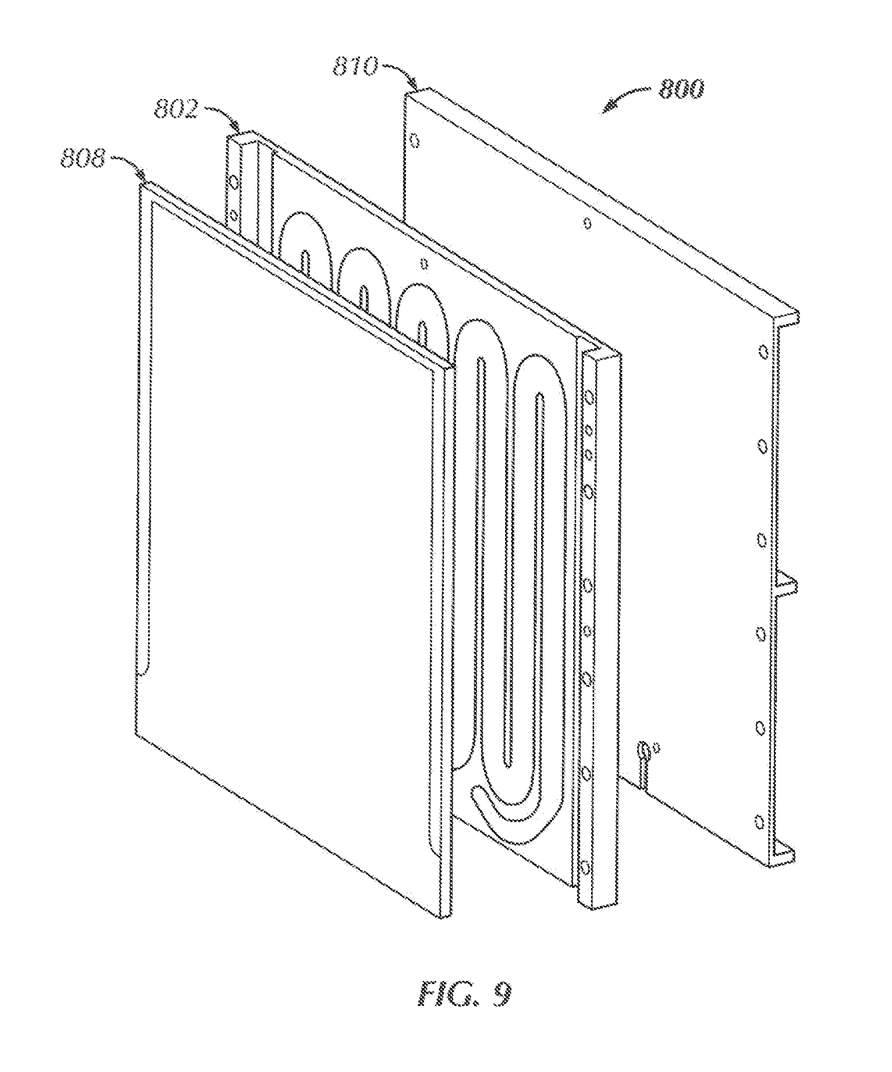
FIG. 9 is an exploded view of a cold plate embodiment.

Left and right backing plates 808, 810 can abut the left and right sides of the separator plate 802 along the entire sides of the separator plate with only the channels 804,806 establishing cavities through which the respective fluids may flow. (An exploded view of 800 is shown, in FIG. 9). Thus, refrigerant may flow through the left channel 804 between the separator plate 802 and the left backing plate 808 and water from the lines L3, L4 in FIG. 1, e.g., from a patient heat exchange pad or from a source of water other than the pad, such as a water reservoir which may act as a thermal storage unit, may flow between the separator plate 802 and the right backing plate 810 through the right channel 806. In this configuration, the cassette slot 34' may be located on the side of the left backing plate 808 that is opposite the separator plate 802 as shown. With this structure, not only can the refrigerant exchange heat with either sterile catheter 12 saline in the cassette or non-sterile fluid from the pad 18, or optionally pad fluid in a cassette, but furthermore in the event that refrigerant is not available or battery power only is available (hence the compressor 22 is effectively offline), water from the cold fluid source 28 (shown in FIG. 1) or a water reservoir (e.g., where the water was previously cooled by the compressor) may be ported to the right channel 806 to provide some heat exchange across the separator plate 802 and left backing plate 808 with the cassette 50 in the slot 34'.

The certain embodiments, various cold assemblies described herein may be assembled by brazing the plates together, e.g., in an oven, and/or e.g. by vacuum brazing. The plates may also or alternatively be connected by mechanical fasteners and sealed with o-rings, and/or a gasket may be utilized.

If desired, the refrigerant may be allowed to warm to heat the present cold, plates when, for example, target temperature is reached, to avoid over-cooling the patient and/or to run a system pump backwards to shorten x-probe equalization stops. Moreover, refrigerant flow may be established or adjusted to maintain, at least some liquid phase of the refrigerant throughout the entire period of time, substantially the entire period of time or part of the time that the refrigerant flows or traverses through the passageway of the cold plate, to promote heat exchange, wherein the refrigerant may exchange heal with working fluid from the intravascular heat exchange catheter and/or the external heat exchange pad.

As discussed above, using the duct 27 in FIG. 1 the patient 18 may be externally warmed for comfort by the exhaust heat from the compressor 22 during internal cooling or to re-warm the patient after cooling. In certain embodiments, heat generated by the system 10, e.g., by the compressor or any other component of the system, may be transferred or directed, onto the surface of a patient to warm the patient before, after or while the patient is cooled with a heat exchange catheter or pad, e.g., to prevent or reduce shivering. In certain variations, heat may be directed onto the patient via a Bairhugger or other hot air blanket or tent used in hospitals to help keep the patient's skin warm. Other mechanisms or ways to warm a patient include but are not limited to: placing or including an electric heating element inside a pad; warming a patient with a radiant heating lamp; directing warm air from a fan on the console or system, which is removing heat from the compressor, onto or toward the surface of a patient; and providing or including a third fluid circuit containing a warming fluid in the system.

While the various embodiments of the COLD PLATE DESIGN IN HEAT EXCHANGER FOR INTRAVASCULAR TEMPERATURE MANAGEMENT CATHETER AND/OR HEAT EXCHANGE FAD axe herein shown and described in detail, the scope of the present invention is to be limited by nothing other than the appended claims. Components included in one embodiment can be used in other embodiments in any appropriate combination. For example, any of the various components described herein and/or depicted in the Figures may be combined, interchanged or excluded from other embodiments.

"A system having at least one of A, B, and C" (likewise "a system having at least one of A, B, or C" and "a system having at least one of A, B, C") includes systems that have A alone, B alone, C alone, A and B together, A and C together, B and C together, and/or A, B, and C together, etc.

What is claimed is:

1. An apparatus comprising:

a plate assembly having a cassette slot configured to receive a membrane assembly of a cassette, with the membrane assembly being configured for containing working fluid from an intravascular heat exchange catheter or heat exchange pad, the plate assembly also including rail receptacles straddling respective sides of the slot and configured for receiving respective side rails of the cassette, wherein at least a first cavity formed inboard of a first one of the rail receptacles, the first cavity having a width at its widest point that is greater than a width of the slot, wherein when the cassette is engaged with the apparatus with the membrane assembly disposed in the slot and the side rails of the cassette disposed in the rail receptacles, a first portion of the membrane assembly that is inboard of a side rail of the cassette can expand into the first cavity when the membrane assembly is filled with working fluid to thereby establish an enlarged fluid passageway along a vertical side edge of the membrane assembly.

2. The apparatus of claim 1, comprising a second cavity formed inboard of a second one of the rail receptacles, the second cavity having a width at its widest point that is greater than a width of the slot.

3. The apparatus of claim 2, wherein the second cavity has a width at its widest point that is less than a width of the first one of the rail receptacles or the second one of the rail receptacles but greater than a width of the slot.

4. The apparatus of claim 1, wherein the first cavity extends substantially an entire length of the first one of the rail receptacles.

5. The apparatus of claim 1, wherein the first cavity is circular or semicircular-shaped.

6. The apparatus of claim 1, wherein a surface of the plate assembly configured to face a received cassette membrane is coated with a non-stick or hydrophobic coating to aid in removal of the cassette after use.

7. The apparatus of claim 1, wherein a surface of the plate assembly configured to face a received cassette membrane is coated with a non-stick or hydrophobic coating to aid in removal of the cassette after use.

8. The apparatus of claim 1, wherein the first cavity is a bulge cavity.

* * * * *

UNITED STATES PATENT AND TRADEMARK OFFICE
CERTIFICATE OF CORRECTION

| | | |
|---|---|---|
| PATENT NO. | : 10,537,465 B2 | Page 1 of 1 |
| APPLICATION NO. | : 14/675504 | |
| DATED | : January 21, 2020 | |
| INVENTOR(S) | : Jeremy Thomas Dabrowiak, Craig Wendell Pendry and Christoph Matthias Pistor | |

It is certified that error appears in the above-identified patent and that said Letters Patent is hereby corrected as shown below:

On the Title Page

Item (57), In the Abstract:
Column 2, Line 4, delete "beat" and insert -- heat --

Signed and Sealed this
Nineteenth Day of May, 2020

Andrei Iancu
*Director of the United States Patent and Trademark Office*